United States Patent [19]

Harvey et al.

[11] 4,307,076

[45] Dec. 22, 1981

[54] TOOTHPASTE COMPOSITIONS

[75] Inventors: Kenneth Harvey, Wilmslow; Stephen T. Connors, Sale, both of England

[73] Assignee: Colgate-Palmolive Company, New York, N.Y.

[21] Appl. No.: 218,594

[22] Filed: Dec. 19, 1980

[30] Foreign Application Priority Data

Dec. 19, 1979 [GB] United Kingdom ............... 43641/79

[51] Int. Cl.³ .......................... A61K 7/16; A61K 31/79
[52] U.S. Cl. ............................................ 424/49; 424/80
[58] Field of Search ..................................... 424/49–58, 424/80

[56] References Cited

U.S. PATENT DOCUMENTS

| | | | |
|---|---|---|---|
| 2,744,049 | 5/1956 | Salzmann et al. | 424/49 |
| 2,783,182 | 2/1957 | Nelson | 424/80 |
| 3,120,469 | 2/1964 | Tamas | 424/49 |
| 3,431,208 | 3/1969 | Bailey | 424/49 |
| 3,840,657 | 10/1974 | Norfleet | 424/54 |
| 3,842,167 | 10/1974 | Block et al. | 424/49 |
| 3,946,108 | 3/1976 | Tomlinson et al. | 424/49 |
| 3,954,962 | 5/1976 | Prussin | 424/49 |
| 3,970,747 | 7/1976 | Barth | 424/52 |
| 4,069,310 | 1/1978 | Harrison | 424/49 |
| 4,223,003 | 9/1980 | Scheller | 424/54 |

FOREIGN PATENT DOCUMENTS

| | | |
|---|---|---|
| 688164 | 2/1953 | United Kingdom . |
| 739936 | 11/1955 | United Kingdom . |
| 741315 | 11/1955 | United Kingdom . |

*Primary Examiner*—Shep K. Rose
*Attorney, Agent, or Firm*—Robert L. Stone; Murray M. Grill; Herbert S. Sylvester

[57] ABSTRACT

A toothpaste composition comprising a vehicle containing about 45–80% by weight of liquid phase, comprising up to about 35% by weight of the toothpaste of sorbitol and at least about 25% by weight of the toothpaste of water and a solid phase including about 3–10% by weight of the toothpaste of gelling agent comprising at least about 3% by weight of the toothpaste of polyvinyl pyrrolidone as an agent to reduce drying and tube plugging.

8 Claims, No Drawings

TOOTHPASTE COMPOSITIONS

This invention relates to a toothpaste composition having desirable rheological characteristics.

A typical toothpaste vehicle is comprised of liquids such as water and humectant and solids such as gelling agents proportioned to provide a creamy or gel-like consistency. When the particular components used are unwisely chosen or their proportion to each other is improper, rheological problems can occur. Such problems include undue hardness or undue liquidity, syneresis or phase separation, drying (especially at the cap end and therefore called "plugging") particularly should the tube be left open etc.

Sorbitol solution in water, typically about 50–80% by weight solution, most often about 70% solution and glycerin are the most commonly used toothpaste humectants. They are generally used in amounts ranging up to about 80% by weight of a toothpaste but most often about 15–40%. Typically water is also present, possibly in amounts of up to 80% by weight of a toothpaste, such as in amounts of about 20–60%.

When sorbitol solution and water (separate from that in which the sorbitol is dissolved) are present in about of up to about 35% by weight and at least about 20% by weight, respectively, after proportioning these liquids with gelling agent drying readily occurs and a hard plug forms at the cap of a toothpaste tube making it very difficult to effectively extrude the paste. Some drying may occur when glycerine is used in place of all or part of the sorbitol solution although the plug which might form would not be as hard.

It is an advantage of this invention that drying of high water content toothpastes containing sorbitol as humectant and gelling agent is reduced or prevented. Other advantages will be apparent upon consideration of the following specification.

In accordance with certain of its aspects this invention relates to a toothpaste composition comprising a vehicle containing about 45–80% by weight of liquid phase comprising up to about 35% by weight (based on the toothpaste) of sorbitol and at least about 25% by weight (based on the toothpaste) of water and a solid phase including about 3–10% by weight (based on the weight of the toothpaste de-gelling agent) at least about 3% by weight (based on the weight of the toothpaste) comprising a polyvinyl pyrrolidone.

In the toothpaste of the present invention up to about 35% by weight of sorbitol is present, typically about 15–35% preferably about 15–25%. If desired, minor amounts (e.g. about 10%) of other humectants such as glycerine or polyethylene glycol of average molecular weight of about 380–420 may also be mixed with sorbitol. Glycerine can reduce (although not eliminate) drying in the absence of polyvinyl pyrrolidone.

Sorbitol is generally employed in water solution, typically about 50–80% by weight solution preferably about 70%. At least about 25% by weight typically about 25–50% preferably about 25–45% of water is present, such high amounts of water have generally been avoided in the past due to a tendancy to dry.

The liquid phase of the toothpaste vehicle, that is humectant and water comprises about 45–80% by weight of the toothpaste, preferably about 55–70%.

The gelling agent may be all or partially polyvinyl pyrrolidone. In addition to polyvinyl pyrrolidone there may be present natural and synthetic gumlike material e.g. Irish Moss, gum tragacanth, methyl cellulose, hydroxyethyl cellulose, sodium carboxymethyl cellulose, starch, carboxyvinyl polymers such as those sold under the trade mark CARBOPOL 937 and 940 and synthetic silicates clays such as those sold under trade mark LAPONITE CP or SP. Polyvinyl pyrrolidone is present in the toothpaste composition in amount of at least about 3% and the total gelling agent is about 3–10% by weight preferably about 5–8%.

In addition to the gelling agent as the solid portion of the toothpaste vehicle, a thickener, such as a thinly divided synthetic colloidal silica sold under the trade marks CAB-O-SIL, AEROSIL D200 and SYLOID 244 and 266, may be present in amount of about 1–5% by weight.

There is distributed in the toothpaste vehicle a dentally acceptable water-insoluble polishing material typically in amount of about 15–50% by weight most preferably about 25–45%. Examples of polishing materials are water-insoluble sodium metaphosphate, potassium metaphosphate, tricalcium phosphate, dehydrated calcium phosphate, anhydrous dicalcium phosphate, calcium phosphate, magnesium orthophosphate, trimagnesium phosphate, calcium carbonate, alumina, hydrated alumina, aluminum silicate, zirconium silicate, silica, sodium aluminosilicate, bentonite, and mixtures thereof. Preferred polishing materials include complex amorphous sodium aluminosilicate, anhydrous alumina, calcium carbonate and dicalcium phosphate. The polishing materials may be used in admixture.

Organic surface-active agents are used in the compositions of the present invention to achieve increased prophylactic action, assist in achieving thorough and complete dispersion of the instant compositions throughout the oral cavity, and render the instant compositions more cosmetically acceptable. The organic surface-active material may be anionic, nonionic, ampholytic, or cationic in nature, and it is preferred to employ as the surface-active agent a detersive material which imparts to the composition detersive and foaming properties. Suitable such detergents are water-soluble salts of higher fatty acid monoglyceride monosulphates, such as sodium lauryl sulphate, alkyl aryl sulphonates, such as sodium dodecyl benzene sulphonate, higher alkyl sulphoacetates, higher fatty acid ester of 1,2-dihydroxy propane sulphonates and the substantially saturated higher acyl amides of lower aliphatic amino carboxylic acid compounds, such as those having 12 to 16 carbons in the fatty acid, alkyl or acyl radicals and the like. Examples of the last mentioned amides are N-lauroyl sarcosine, and the sodium, potassium and ethanolamine salts of N-lauroyl, N-myristoyl or N-palmitoyl sarcosine which should be substantially free from soap or similar higher fatty acid material which tends to substantially reduce the effect of these compounds. The use of these sarcosinate compounds in dentifrice compositions of the present invention is particularly advantageous since these materials exhibit a prolonged and marked effect in the inhibition of acid formation in the oral cavity due to carbohydrates breakdown in addition to exerting some reduction in the solubility of tooth enamel in acid solutions.

Other particularly suitable surface-active materials include nonionic agents such as condensates of sorbitan monostearate with approximately 60 moles of ethylene oxide, consensates of ethylene oxide with propylene oxide condensates of propylene glycol (available under the trade mark PLURONICS) and amphoteric agents such as quaternized imidazol derivatives which are available under the trade mark MIRANOL such as MIRANOL C₂M. Cationic surface-active germicides and antibacterial compounds such as diisobutylphenoxyethoxyethyl dimethyl benzyl ammonium chloride, benzyl dimethyl stearyl ammonium chloride, tertiary amines having one fatty alkyl group (of from 12 to 18 carbon atoms) and two (poly) oxyethylene groups attached to the nitrogen (typically containing a total of from about 2 to 50 ethanoxy groups per molecule) and salts thereof with acids and compounds of the structure

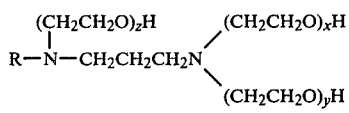

where R is a fatty alkyl group containing from about 12 to 18 carbon atoms, and x, y and z total 3 or higher, as well as salts thereof with mineral or organic acids, may also be used. It is preferred to use from about 0.05 to 5% by weight of the foregoing surface-active materials in the instant oral preparations.

A fluorine-providing compound may be present. This compound may be slightly soluble in water or may be fully water-soluble. It is characterized by its ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, a copper fluoride such as cuprous fluoride zinc fluoride, a tin fluoride such as stannous fluoride or stannous chlorofluoride, barium fluoride, sodium fluorosilicate, ammonium fluorosilicate, sodium fluorozirconate, sodium monofluorophosphate, aluminium mono- and difluorophosphate. Alkali metal and tin fluorides, such as sodium and stannous fluorides, sodium monofluorophosphate and mixtures thereof, are preferred. A mixture of sodium fluoride and sodium monofluorophosphate is particularly desirable. In the toothpaste an amount of fluorine-providing compound which releases a maximum of about 1% by weight of the toothpaste is satisfactory. Any suitable minimum of such compound may be used, but it is preferable to employ sufficient compound to release from about 0.005% to 1%, and preferably about 0.1% of fluoride ion. Typically, in the cases of alkali metal fluorides and stannous fluoride, this component is present in an amount up to 2% by weight, based on the weight of the toothpaste, and preferably in the range of from 0.05% to 1%. In the case of sodium monofluorophosphate, the compound may be present in an amount up to 7.6% by weight, more typically 0.76%. When present in mixture the ratio of sodium monofluorophosphate to sodium fluoride is desirably about 1:1 to 3:1 based on fluorine provided by each.

Any suitable flavouring or sweetening material may also be employed. Examples of suitable flavouring constituents are flavouring oils e.g. oils of spearmint, peppermint, wintergreen, sassafras, clove, sage, eucalyptus, marjoram, cinnamon, lemon, orange, and methyl salicylate. Suitable sweetening agents include sucrose, lactose, maltose, sorbitol, sodium cyclamate, perillartine and sodium saccharin. Suitably, flavouring and sweetening agents may together comprise from 0.01% to 5% or more of the preparations.

Various other materials may be incorporated in the oral preparations of this invention. Examples thereof are colouring or whitening agents, preservatives, silicones, chlorophyll compounds, ammoniated materials such as urea, diammoniumphosphate and mixtures thereof, and other constituents. These adjuvants are incorporated in the instant compositions in amounts which do not substantially adversely affect the properties and characteristics desired and are selected and used in proper amount depending upon the particular type of preparation involved.

The dental cream typically has a pH (determined directly on the cream) of about 4 to 10.5, preferably about 6–10. If desired, the pH may be adjusted with an acidic material, such as benzoic or citric acid, or an alkaline material, such as sodium hydroxide, to achieve a particular value. Buffering agents, e.g. phosphate buffers, may be used.

The dental cream may be prepared by adding humectant to water and blending therewith the gelling agent and thereafter the polishing material.

In evaluating toothpastes of the present invention, viscosity may be determined with the Universal Testing Instrument (table model) manufactured by Instron Ltd, High Wycombe, England. Viscosity comprising can also be determined within an extension rheometer.

The following specific example is further illustrative of the nature of the present invention but it is understood that the invention is not limited thereto. The composition is prepared in the usual manner and all amounts and proportions are by weight unless otherwise specified.

EXAMPLE

|  | A | B | C |
|---|---|---|---|
| Sorbitol (70%) | 16.00 | 22.00 | 20.00 |
| Polyvinyl Pyrrolidone | 6.00 | 3.00 | — |
| Sodium Carboxymethyl Celluose | 1.10 | 1.10 | 1.10 |
| Sodium Saccharin | 0.20 | 0.20 | 0.18 |
| Titanium Dioxide | 0.40 | 0.40 | 0.40 |
| Sodium Monofluorophosphate | 0.80 | 0.80 | 0.80 |
| Anhydrous Alumina | 10.00 | 10.00 | 10.00 |
| Sodium Aluminosilicate (About 7% Alumina) | 20.00 | 20.00 | 20.00 |
| Sodium Lauryl Sulphate | 1.77 | 1.77 | 1.50 |
| Flavour | 1.10 | 1.10. | 1.00 |
| Water | 42.63 | 39.63 | 45.00 |

Toothpaste compositions A and B and extrude easily after 7, 16, 24 and 31 hours of being left open, whereas toothpast C, quickly dries and forms into a hard plug within 7 hours of being left opened and is difficult to extrude.

Although this invention has been described with regard to specific example, it will be apparent to one skilled in the art that various modifications may be made thereto which fall within its scope.

We claim:

1. A tubed toothpaste composition comprising a vehicle containing about 45–80% by weight of liquid phase, consisting essentially of from about 15% up to about 35% by weight of the toothpaste of sorbitol and at least about 25% by weight of the toothpaste of water and a solid phase including about 3–10% by weight of the toothpaste of gelling agent wherein drying readily occurs and a hard plug forms at the cap end of a toothpaste tube particularly when the tube is permitted to remain open, typically within about 7 hours of being left open, making it very difficult to effectively extract the paste from the tube, the improvement comprising said toothpaste containing in said gelling agent at least about 3% by weight of the toothpaste of polyvinyl pyrrolidone.

2. A toothpaste composition claimed in claim 1 wherein said sorbitol is present in amount of about 15-25% by weight.

3. A toothpaste composition claimed in claim 1 wherein said water is present in amount of about 25-50% by weight.

4. A toothpaste composition claimed in claim 2 wherein said water is present in amount of about 25-45% by weight.

5. A toothpaste composition claimed in claim 1, wherein about 15-50% by weight of a dentally acceptable water-insoluble polishing agent is present.

6. A toothpaste composition claimed in claim 5 wherein said polishing agent is sodium aluminosilicate.

7. A toothpaste composition claimed in claim 1 wherein about 3-6% by weight of polyvinyl pyrrolidone is present.

8. A toothpaste composition claimed in claim 1 wherein said gelling agent additionally comprises sodium carboxymethyl cellulose.

* * * * *